United States Patent [19]
Merkle et al.

[11] Patent Number: 4,996,327
[45] Date of Patent: Feb. 26, 1991

[54] PREPARATION OF PYRAZOLE AND ITS DERIVATIVES

[75] Inventors: Hans R. Merkle, Ludwigshafen; Erich Fretschner, Neckarsteinach, both of Fed. Rep. of Germany

[73] Assignee: BASF Aktiengesellschaft, Ludwigshafen, Fed. Rep. of Germany

[21] Appl. No.: 534,270

[22] Filed: Jun. 7, 1990

[30] Foreign Application Priority Data

Jun. 10, 1989 [DE] Fed. Rep. of Germany ....... 3918979

[51] Int. Cl.$^5$ ........................................... C07D 231/12
[52] U.S. Cl. .................................... 548/373; 548/378
[58] Field of Search ............................... 548/373, 378

[56] References Cited

U.S. PATENT DOCUMENTS 4,424,364  1/1984  Goetz et al. .................... 548/373
4,434,292  2/1984  Heinemann et al. ............. 548/373

OTHER PUBLICATIONS

Wiley, Pyrazoles, Pyrazolines, Pyrazolidines, Indazoles and Condensed Rings, (1967) pp. 41 and 48.

Primary Examiner—Robert W. Ramsuer
Attorney, Agent, or Firm—Keil & Weinkauf

[57] ABSTRACT

Pyrazole and its derivatives are prepared by dehydrogenating 2-pyrazoline or its derivatives by a process in which the reaction is carried out using sulfuric acid in the presence of iodine or of an iodine compound at from 50° to 250° C.

5 Claims, No Drawings

PREPARATION OF PYRAZOLE AND ITS DERIVATIVES

The present invention relates to a novel process for the preparation of pyrazole

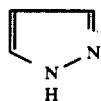

and its derivatives from 2-pyrazoline

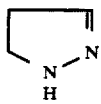

or its derivatives.

It is known that 2-pyrazoline can be dehydrogenated to pyrazole using chlorine, alkali metal or alkaline earth metal hypochlorites (DE-A No. 30 35 395), using sulfur or selenium (DE-A No. 30 29 160) or using aqueous hydrogen peroxide (DE-A No. 34 15 385). Furthermore, the thermal gas-phase dehydrogenation of 2-pyrazoline over palladium or platinum catalysts (DE-A No. 32 09 148) and the thermolysis of N-sulfonyl-2-pyrazoline to pyrazole (DE-A No. 30 35 394) are known.

However, these processes are technically unsatisfactory, because they either require the use of very aggressive oxidizing agents or expensive catalysts, or involve the formation of toxic byproducts, such as hydrogen sulfide or hydrogen selenide, or are unsuitable for the preparation of N-substituted pyrazoles.

It is an object of the present invention to make pyrazole and its derivatives available in a technically simpler and more economical manner.

We have found that this object is achieved by a process for the preparation of pyrazole

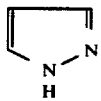

and its derivatives by dehydrogenation of 2-pyrazoline

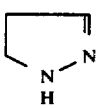

or its derivatives, wherein the reaction is carried out using sulfuric acid in the presence of iodine or of an iodine compound at from 50° to 250° C.

The process is presumably based on the principle that the iodine acts as a dehydrogenating agent and is converted to hydrogen iodide in the course of the reaction. The hydrogen iodide can then be oxidized back to iodine by the sulfuric acid, thus explaining the fact that it is possible to manage with catalytic amounts of iodine or of the iodine compound.

In this reaction, iodine or the iodine compound is generally used in amounts of from 0.01 to 10, preferably from 0.05 to 5, in particular from 0.1 to 2, mol % per mol of 2-pyrazoline.

If an iodine compound is used from the outset, it is to be assumed that iodine is initially formed, this being followed by the cycle described.

From the catalysis cycle described above, it is evident that the sulfuric acid acts as an oxidizing agent for hydrogen iodide and should be present in an appropriate concentration of not less than 30, preferably from 45 to 95, % by weight. A corresponding concentration of sulfuric acid can also be achieved under the reaction conditions by continuously removing excess water from the reaction mixture.

In addition to elemental iodine, other suitable catalysts are iodine compounds, such as hydrogen iodide, alkali metal and alkaline earth metal iodides, such as lithium iodide, sodium iodide, potassium iodide, cesium iodide, magnesium iodide and calcium iodide, and other metal iodides; it is also possible to use other inorganic iodine compounds, such as alkaline earth metal and alkali metal hypoiodides, iodites, iodates and periodates, or organic iodine compounds, such as alkyl iodides, eg. methyl iodide.

The dehydrogenation is generally carried out under atmospheric pressure at from 50° to 250° C., preferably from 70° to 200° C., in particular from 90° to 180° C.

However, it is also possible to carry out the reaction under superatmospheric pressure in sulfuric acid of a lower concentration or at a correspondingly higher temperature or under reduced pressure in more highly concentrated sulfuric acid or at a correspondingly lower temperature.

The reaction is generally carried out by combining all reactants in the reaction vessel and then heating them together to the reaction temperature. However, the reactants may also be introduced separately or as a mixture into a preheated reaction vessel, or some of the reactants may be initially taken at the reaction temperature and the other reactant or reactants added.

The water distilled off and removed from the reaction contains the major part of the iodide used, in the form of hydrogen iodide, which can be recycled into the reaction mixture.

After the reaction mixture has been cooled, the pyrazole derivative crystallizes as the sulfate.

For working up, the resulting reaction mixture is neutralized, for example with sodium hydroxide solution, ammonia or another inorganic or organic base, and the neutral mixture is extracted several times with an inert organic, water-immiscible solvent. Drying the organic extract and evaporation to dryness give the corresponding pyrazoles in a purity of 85-95%, and these pyrazoles can be distilled or recrystallized to improve the purity.

The novel process is suitable for the preparation of pyrazole and substituted pyrazoles from the corresponding 2-pyrazoline derivatives, in particular those of the general formula Ia

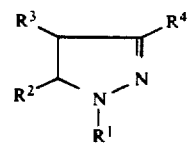

where $R^1$ to $R^4$ are each hydrogen or organic carbon radicals, and experience to date indicates that the nature of the substituents has little effect.

Suitable radicals $R^1$ to $R^4$ in addition to hydrogen are preferably one to three of the following groups: $C_1$-$C_8$-alkyl, in particular $C_1$-$C_4$-alkyl, such as methyl, ethyl, propyl, 1-methylethyl, butyl, 1-methylpropyl, 2-methylpropyl and 1,1-dimethylethyl; $C_3$-$C_8$-cycloalkyl, in particular cyclopentyl, cyclohexyl and cycloheptyl; aralkyl, in particular phenyl-substituted $C_1$-$C_4$-alkyl as mentioned above; aryl, in particular phenyl.

These radicals can in turn be interrupted by heteroatoms, such as nitrogen, oxygen and sulfur, or may carry further inert substituents, such as halogen, nitro, sulfonyl, $C_1$-$C_4$-alkylsulfonyl, arylsulfonyl and carboxyl, provided that they are inert under the reaction conditions.

The 2-pyrazolines used as starting compounds are known or are obtainable by known methods, condensation of a compound having an acrolein or vinyl alkyl ketone structure and a hydrazine being particularly recommended (Behr et al., The Chemistry of Heterocyclic Compounds, Vol 22, Chapter 7; DE-A No. 3423930).

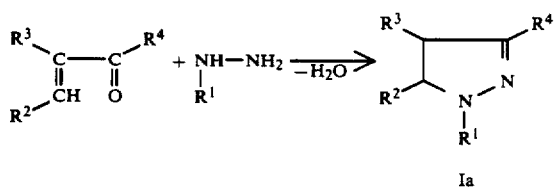

This condensation is usually carried out in an inert organic solvent or in aqueous solution in the presence of a base or acid.

With regard to the novel process, it is particularly preferable to carry out even this condensation reaction using sulfuric acid, the dehydrogenation catalyst iodine or the iodine compound being added at the outset and the intermediate of the 2-pyrazoline not being isolated.

In this case, the reaction is advantageously carried out by a procedure in which from 0.65 to 1.25 mol equivalents of the corresponding acrolein/vinyl alkyl ketone derivative are reacted with 1 mol equivalent of the hydrazine under the conditions described above, in sulfuric acid, in the presence of iodine or of an iodine compound.

Instead of the vinyl alkyl ketones, it is also possible to use their precursors, for example β-hydroxyethyl alkyl ketones.

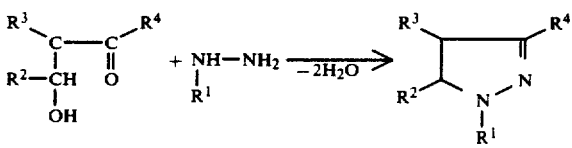

It is also possible to prepare the β-hydroxyethyl ketones themselves in situ, for example from acetone and formaldehyde.

Another possible method for preparing the 2-pyrazolines is to react a compound having a glycerol structure and a corresponding hydrazine.

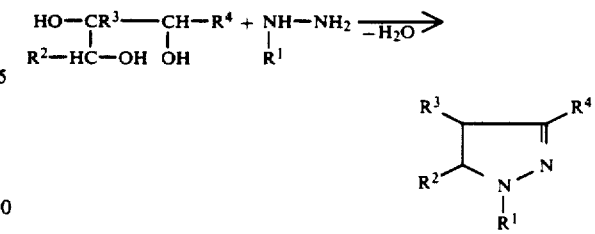

As described above for the condensation of the acrolein/vinyl alkyl ketone derivative with hydrazine derivatives, the condensation of the glycerol-analogous compounds with hydrazine derivatives can also be carried out in sulfuric acid in the presence of iodine or of the iodine compound, the intermediate of the 2-pyrazoline being directly dehydrogenated at a suitable reaction temperature.

PROCESS EXAMPLES

1. Conversion of 2-pyrazoline to pyrazole

A mixture of 145.8 g of a 48% strength by weight aqueous solution of pyrazoline (1 mol) and 2 g of sodium iodide (0.0134 mol) was added to 270 g of 80% strength by weight sulfuric acid in the course of 90 min at 155° C. By distilling off water, the temperature of the reaction mixture was kept at 155° C. When the addition was complete, the mixture was left for a further 30 min at 155° C. and then cooled to 60° C.

The reaction mixture thus obtained was neutralized with 20% strength sodium hydroxide solution. The pyrazole was obtained by extracting the reaction mixture with an inert water-immiscible organic solvent in the conventional manner.

Yield 69.5 g of a solid of 93.1% purity (GC analysis), corresponding to 95.2%, based on the 2-pyrazoline used.

2. General method for the preparation of pyrazoles from hydrazines and acroleins, vinyl alkyl ketones or β-hydroxyethyl alkyl ketones or glycerols 2.1

Hydrazine hydrate or a hydrazine $H_2N$-$NHR^1$ (A-3), an acrolein/vinyl alkyl ketone $R^2CH=CR^3$—CO—$R^4$ (A-1), or a β-hydroxyethyl alkyl ketone $R^2$—CH(OH)—$CR^3(H)$—CO—$R^4$ (A-1*) or a glycerol $R^2$—CH(OH)—$CR^3(OH)CH(OH)$—$R^4$ (A-2) and a mol %, based on the hydrazine used, of an iodine compound (catalyst) were added simultaneously or in succession to n g of a c % strength by weight sulfuric acid, while cooling. The mixture thus obtained was then heated at T° C. for t hours with removal of water by distillation.

After working up in a conventional manner, y %, based on the hydrazine or its derivative used, of pyrazole were obtained. 2.2

An acrolein/vinyl alkyl ketone (A-1) or a β-hydroxyethyl alkyl ketone $R^2$—CH(OH)—$CR^3(H)$—CO—$R^4$ (A-1*) or a glycerol (A-2), hydrazine hydrate or a hydrazine (A-3) and a mol %, based on the hydrazine used, of an iodine compound (catalyst) were added simultaneously or in succession to n g of a c % strength by weight sulfuric acid at T° C. After a total reaction time of t hours (addition and subsequent stirring), the mixture was worked up in a conventional manner. 2.3

Hydrazine hydrate or a hydrazine (A-3) and a mol %, based on the hydrazine used, of an iodine compound (catalyst) were added simultaneously or in succession to n g of a c % strength by weight sulfuric acid, while cooling. The mixture thus obtained was heated to T° C., and an acrolein/vinyl alkyl ketone or a β-hydroxyethyl alkyl ketone R²—CH(OH)—CR³(OH)—CR³(H)—CO—R⁴ (A-1*) or a glycerol (A-2) was added at this temperature. After a reaction time of t hours (addition of A-1, A-1 and A-2 and subsequent stirring), the mixture was worked up in a conventional manner.

The details of the experiments carried out are shown in the Table below.

creased to 153° C. in the course of 60 minutes while distilling off water, after which stirring was continued for a further 45 minutes at this temperature. A total of 330 g of water were distilled off.

After neutralization with 25% sodium hydroxide solution, extraction was carried out using 1,2-dichloroethane. The combined 1,2-dichloroethane extracts were dried and evaporated down. 28 g of a brown oil whose gas chromatogram indicated 80% by area of 3-methyl-

TABLE $$R^2-CH=CR^3-CO-R^4 \text{ or } R^2-CH-CR^3-CO-R^4 \text{ or } R^2-CH-CR^3-CH-R^4 \xrightarrow{H_2N-NHR^2} \underset{A-3}{} $$
$$\phantom{xxxxxxxxxxxxxxxxxxxxxxxxx}\underset{OH}{|}\phantom{xxxxxxxxxxxx}\underset{OH\ OH\ OH}{|\ |\ |}$$
$$\phantom{xxxxxxx}\text{A-1}\phantom{xxxxxxxxxxxxxx}\text{A-1*}\phantom{xxxxxxxxxxxxxxxxx}\text{A-2}$$

| Example No. | A-1 or A-2 R² | R³ | R⁴ | mol | A-3 R¹ | mol | H₂SO₄/H₂O n[g]⁽ᶜ⁾ | c | Catalyst Art | a⁽ᶜ⁾ | t[h] | T[°C.] | Pyrazole y[%]⁽ᶜ⁾ | R¹ | R² | R³ | R⁴ | Process Variant |
|---|---|---|---|---|---|---|---|---|---|---|---|---|---|---|---|---|---|---|
| 2⁽ᵇ⁾ | H | H | H | 1,1 | H | 1.0 | 449.6 | 47.9 | NaI | 1.34 | 4.5 | 145–155 | 86.6 | H | H | H | H | 2.1 |
| 3⁽ᵇ⁾ | H | H | H | 1,1 | H | 1.0 | 269.6 | 80.0 | NaI | 0.67 | 2.5 | 155 | 91.8 | H | H | H | H | 2.2 |
| 4⁽ᵃ⁾ | H | H | H | 1,2 | H | 1.0 | 410 | 70.2 | NaI | 0.67 | 3.0 | 120 | 76.7 | H | H | H | H | 2.3 |
| 5⁽ᵃ⁾ | H | H | H | 1,2 | H | 1.0 | 392.2 | 50.0 | NaI | 0.67 | 2.5 | 155 | 82.0 | H | H | H | H | 2.1 |
| 6⁽ᵇ⁾ | H | H | H | 1,1 | H | 1.0 | 431.2 | 50.0 | NaIO₃ | 0.66 | 4.0 | 155 | 80.8 | H | H | H | H | 2.1 |
| 7⁽ᵇ⁾ | H | H | H | 1,1 | H | 1.0 | 431.2 | 50.0 | CH₃I | 0.7 | 4.0 | 155 | 19.7 | H | H | H | H | 2.1 |
| 8⁽ᵇ⁾ | H | H | H | 1,1 | H | 1.0 | 269.6 | 80.0 | HI | 0.66 | 2.5 | 155 | 82.3 | H | H | H | H | 2.2 |
| 6⁽ᵃ⁾ | H | H | H | 1,1 | H | 1.0 | 431.2 | 50.0 | J₂ₗ | 0.17 | 2.0 | 155 | 78.5 | H | H | H | H | 2.2 |
| 10⁽ᵃ⁾ | H | H | H | 1,2 | CH₃ | 1.0 | 420.2 | 70.0 | NaI | 1.34 | 2.0 | 118 | 57.1 | CH₃ | H | H | H | 2.3 |
| 11⁽ᵃ⁾ | H | CH₃ | H | 2,4 | H | 2.0 | 410.0 | 70.2 | NaI | 0.67 | 3.0 | 115–130 | 85.4 | H | H | CH₃ | H | 2.3 |
| 12⁽ᵃ⁾ | CH₃ | H | H | 1,2 | H | 1.0 | 410.0 | 70.2 | NaI | 0.67 | 3.0 | 115–130 | 75.6 | H | CH₃ | H | H | 2.3 |
| 13⁽ᵃ⁾ | H | H | CH₃ | 1,17 | H | 1.0 | 410.0 | 70.2 | NaI | 0.67 | 2.5 | 115–130 | 91.2 | H | H | H | CH₃ | 2.3 |
| 14⁽ᵃ⁾ | H | CH₃ | H | 1,2 | CH₃ | 1.0 | 410.0 | 70.2 | NaI | 0.67 | 3.0 | 130 | 59.4 | CH₃ | H | CH₃ | H | 2.3 |
| 15⁽ᵃ⁾* | H | H | CH₃ | 1,1 | H | 1.0 | 431.2 | 50.0 | NaI | 0.67 | 3.0 | 100–155* | 79.5 | H | H | H | CH₃ | 2.3 |

⁽ᵃ⁾from A-1;
⁽ᵇ⁾from A-2;
⁽ᵃ⁾*from A-1*;
⁽ᶜ⁾based on 1 mol A-3

EXAMPLE 15

Preparation of 3-methylpyrazole from 3-ketobutan-1-ol 50 g (1 mol) of hydrazine hydrate and 1 g of sodium iodide were added to 431.2 g of 50% strength sulfuric acid in the course of 15 minutes at room temperature. Thereafter, the mixture was heated to 100° C. and 193.6 g (1.1 mol) of 50% strength aqueous 3-ketobutan-1-ol solution were added dropwise in the course of 60 minutes. By distilling off water, a reaction temperature of 155° C. was achieved to the end of the addition, after which stirring was continued at this temperature for 60 minutes. A total of 350 g of water were distilled off.

After cooling to 70° C., the mixture was neutralized with 15% strength sodium hydroxide solution and extracted with 1,2-dichloroethane. The combined organic extracts were dried over sodium sulfate and filtered, and the filtrate was evaporated down in a rotary evaporator. 90.4 g of a dark brown oil were obtained, which was distilled under reduced pressure to give 65.2 g of 3-methylpyrazole of boiling point 108° C./35, which was identified by comparison with the authentic material using GC.

EXAMPLE 16

50 g (1 mol) of hydrazine hydrate were added to 431.2 g (2.2 mmol) of 50% strength sulfuric acid, the reaction temperature increasing to 90° C. After the addition of 1 g of sodium iodide, a solution of 90.4 g (1.1 mol) of 36.5% strength formalin solution in 63.8 g (1.1 mol) of acetone was added dropwise in the course of 30 minutes at 90° C. The reaction temperature was inpyrazole were obtained.

We claim:

1. A process for the preparation of pyrazole

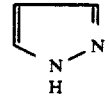

and its derivatives by dehydrogenation of 2-pyrazoline

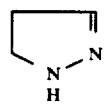

or its derivatives, wherein the reaction is carried out using sulfuric acid in the presence of iodine or of an iodine compound at from 50° to 250° C.

2. A process for the preparation of an unsubstituted or substituted pyrazole derivative as claimed in claim 1, wherein a 2-pyrazoline derivative of the formula Ia

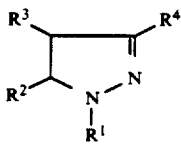

where $R^1$ to $R^4$ are unsubstituted or substituted by inert groups and are each $C_1$–$C_8$-alkyl, phenyl-substituted $C_1$–$C_4$-alkyl or aryl or may furthermore be hydrogen, is dehydrogenated.

3. A process for the preparation of pyrazole and its derivatives as claimed in claim 1, wherein the 2-pyrazoline or a derivative thereof is produced in situ in the reaction medium by reacting glycerol, acrolein, a vinyl alkyl ketone or a β-hydroxyethyl alkyl ketone or a derivative thereof with hydrazine or a hydrazine derivative.

4. A process as claimed in claim 1, wherein the dehydrogenation is carried out in the presence of from 0.01 to 10 mol equivalents, based on the pyrazoline or the hydrazine, of iodine or of an iodine compound.

5. A process as claimed in claim 1, wherein the reaction is carried out using from 30 to 99% strength by weight sulfuric acid.

* * * * *